US010568754B2

(12) United States Patent
Valdes et al.

(10) Patent No.: US 10,568,754 B2
(45) Date of Patent: Feb. 25, 2020

(54) PROTECTIVE APPARATUS FOR USE IN GASTROINTESTINAL TRACT

(71) Applicant: BOSTON SCIENTIFIC SCIMED, INC., Maple Grove, MN (US)

(72) Inventors: Caleb A. Valdes, Lowell, MA (US); Nigel Slater, Ashland, MA (US); John Modlish, Groveland, MA (US); Thomas G. Hirte, Litchfield, NH (US); Cristina Tessier, Ayer, MA (US); Sweta Pherwani, Framingham, MA (US); Paul Mannion, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 330 days.

(21) Appl. No.: 15/594,470

(22) Filed: May 12, 2017

(65) Prior Publication Data
US 2017/0325983 A1  Nov. 16, 2017

Related U.S. Application Data

(60) Provisional application No. 62/336,105, filed on May 13, 2016.

(51) Int. Cl.
*A61F 5/00* (2006.01)
*A61F 2/90* (2013.01)

(52) U.S. Cl.
CPC .............. *A61F 5/0036* (2013.01); *A61F 2/90* (2013.01)

(58) Field of Classification Search
CPC ... A61F 5/0036; A61F 2250/0039; A61F 2/04
See application file for complete search history.

(56) References Cited

U.S. PATENT DOCUMENTS

| | | | |
|---|---|---|---|
| 6,626,936 B2 | 9/2003 | Stinson | |
| 7,101,392 B2 | 9/2006 | Heath | |
| 7,462,192 B2 | 12/2008 | Norton et al. | |
| 7,655,039 B2 | 2/2010 | Leanna et al. | |
| 7,731,742 B2 | 6/2010 | Schlick et al. | |
| 7,837,645 B2 | 11/2010 | Bessler et al. | |
| 8,002,731 B2 | 8/2011 | Weitzner et al. | |
| 8,162,871 B2 | 4/2012 | Levine et al. | |
| 8,372,134 B2 | 2/2013 | Schlick et al. | |
| 8,702,642 B2 | 4/2014 | Belhe et al. | |
| 8,801,647 B2 | 8/2014 | Melanson et al. | |
| 8,870,806 B2 | 10/2014 | Levine et al. | |
| 9,278,020 B2 | 3/2016 | Levine et al. | |
| 2003/0040804 A1 | 2/2003 | Stack et al. | |
| 2003/0236514 A1 | 12/2003 | Schwarz | |
| 2006/0190075 A1 | 8/2006 | Jordan et al. | |
| 2006/0276887 A1 | 12/2006 | Brady et al. | |

(Continued)

*Primary Examiner* — Leslie R Deak
(74) *Attorney, Agent, or Firm* — Seager, Tufte & Wickhelm, LLP

(57) ABSTRACT

An apparatus may be used after a surgical procedure to protect against leaks and to separate healing tissue from foreign materials such as nutritional contents. In some cases the apparatus may be easily delivered to a surgical site before, during or after a surgical procedure such as gastric bypass surgery, but this is only an example. The apparatus may include expandable anchors at either end and a collapsible central portion extending between the two expandable anchors.

20 Claims, 11 Drawing Sheets

(56) References Cited

U.S. PATENT DOCUMENTS

| | | |
|---|---|---|
| 2009/0012544 A1 | 1/2009 | Thompson et al. |
| 2010/0121461 A1 | 5/2010 | Sobrino-Serrano et al. |
| 2010/0256775 A1 | 10/2010 | Belhe et al. |
| 2011/0087146 A1 | 4/2011 | Ryan et al. |
| 2014/0081416 A1 | 3/2014 | Clerc et al. |
| 2014/0243950 A1* | 8/2014 | Weiner ..................... A61F 2/04 623/1.12 |
| 2015/0374484 A1 | 12/2015 | Hingston et al. |
| 2016/0058914 A1 | 3/2016 | Bangera et al. |
| 2016/0081832 A1* | 3/2016 | Hingston .............. A61F 5/0076 623/23.65 |
| 2017/0348129 A1* | 12/2017 | Hingston .............. A61F 5/0036 |

\* cited by examiner

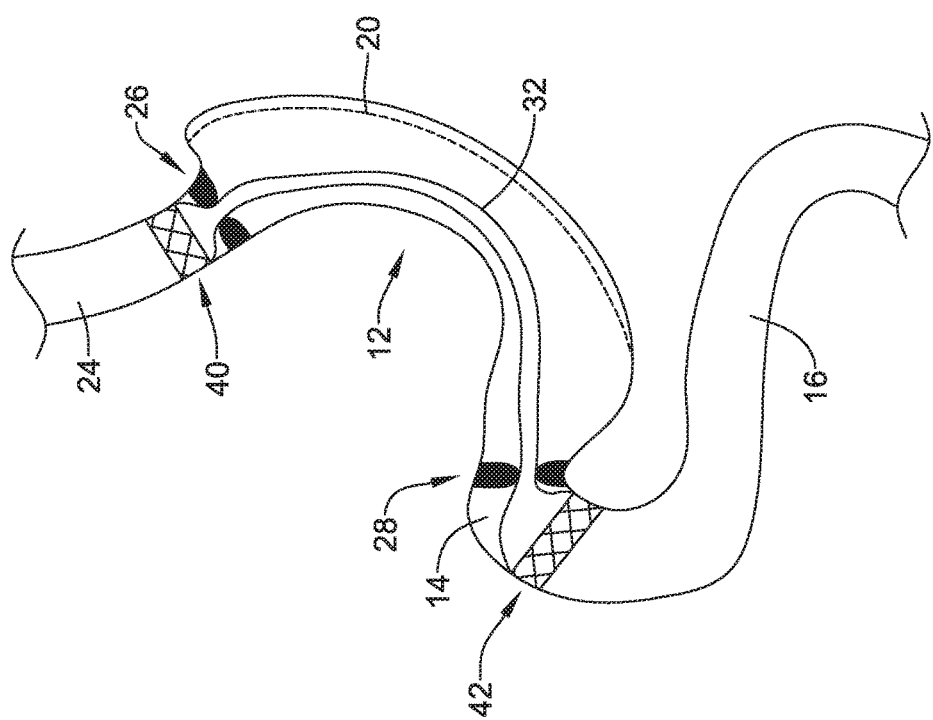

PROTECTIVE APPARATUS FOR USE IN GASTROINTESTINAL TRACT

CROSS-REFERENCE TO RELATED APPLICATIONS

This application claims priority to U.S. Provisional Application No. 62/336,105, filed May 13, 2016, the entire disclosure of which is herein incorporated by reference.

TECHNICAL FIELD

The disclosure is directed to devices for protecting portions of the gastrointestinal tract. More particularly, the disclosure is directed to devices that are configured to extend through the stomach and protect against leaks subsequent to bariatric procedures.

BACKGROUND

Wounds may develop within the gastrointestinal system for a variety of reasons. For example, bariatric surgical procedures create staple lines that may be prone to leakage. In some cases, the presence of materials such as nutritional contents can interfere with healing of the staple lines. In some instances, the presence of nutritional contents can irritate healing tissue and can lead to infection. It may be helpful to protect the healing staple line from materials such as nutritional contents. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and uses thereof. For example, the disclosure is directed to an apparatus that can be used after a surgical procedure to protect against leaks and to separate healing tissue from foreign materials such as nutritional contents. In some cases the apparatus may be easily delivered to a surgical site before, during or after a surgical procedure such as gastric bypass surgery, but this is only an example.

An apparatus for protecting against leaks after a surgical procedure on a stomach is disclosed. The apparatus is configured to extend through the stomach once implanted and includes an elongate collapsible tubular member having a proximal region and a distal region and a collapsible lumen extending therethrough. An expandable proximal anchor is secured to the proximal region of the elongate collapsible tubular member and is configured to anchor at a first position above the lower esophageal sphincter. An expandable distal anchor is secured to the distal region of the elongate collapsible tubular member and is configured to anchor at a second position below the pylorus sphincter. The elongate collapsible tubular member, once implanted, extends through the lower esophageal sphincter such that the lower esophageal sphincter can close the elongate collapsible tubular member proximate the lower esophageal sphincter by collapsing the collapsible lumen. The elongate collapsible tubular member extends through the pylorus sphincter such that the pylorus sphincter can close the elongate collapsible tubular member proximate the pylorus sphincter by collapsing the collapsible lumen.

Alternatively or additionally to any of the embodiments above, the expandable proximal anchor includes a braided stent and a covering disposed over at least part of the braided stent.

Alternatively or additionally to any of the embodiments above, the expandable distal anchor includes a braided stent and a covering disposed over at least a part of the braided stent.

Alternatively or additionally to any of the embodiments above, the apparatus further includes a removal tether extending around a circumference of the expandable proximal anchor.

Alternatively or additionally to any of the embodiments above, the apparatus further includes a removal tether extending around a circumference of the expandable distal anchor.

Alternatively or additionally to any of the embodiments above, the apparatus is bio-absorbable.

Alternatively or additionally to any of the embodiments above, the apparatus further includes a wire support extending at least partially along the elongate collapsible tubular member.

Alternatively or additionally to any of the embodiments above, the wire support extends from the expandable proximal anchor to the expandable distal anchor.

Alternatively or additionally to any of the embodiments above, the wire support is embedded in the elongate collapsible tubular member.

Alternatively or additionally to any of the embodiments above, the wire support extends helically along the elongate collapsible tubular member.

Alternatively or additionally to any of the embodiments above, the elongate collapsible tubular member is formed of a polymer having a Shore durometer hardness of less than 60 A.

Alternatively or additionally to any of the embodiments above, the expandable proximal anchor and the expandable distal anchor each include a wider tissue engagement portion and a narrower portion configured for securement to the elongate collapsible tubular member.

An apparatus for protecting against leaks within a portion of a patient's gastrointestinal tract is disclosed. The gastrointestinal tract includes a sphincter that is configured to reversibly close the gastrointestinal tract proximate the sphincter. The apparatus includes an elongate collapsible tubular member having a first end and a second end and a collapsible lumen extending therethrough. A first anchor is secured near the first end of the elongate collapsible tubular member and is configured to anchor at a position upstream from the sphincter. A second anchor is secured near the second end of the elongate collapsible tubular member and is configured to anchor at a position downstream from the sphincter. The elongate collapsible tubular member extends through the sphincter such that the sphincter can close the elongate collapsible tubular member proximate the sphincter by collapsing the collapsible lumen.

Alternatively or additionally to any of the embodiments above, the sphincter is a lower esophageal sphincter, and the first anchor is configured to be positioned upstream of the lower esophageal sphincter and the second anchor is configured to be positioned downstream of the lower esophageal sphincter such that the elongate collapsible tubular member extends through the lower esophageal sphincter.

Alternatively or additionally to any of the embodiments above, the sphincter is a pylorus sphincter, and the first anchor is configured to be positioned upstream of the pylorus sphincter and the second anchor is configured to be positioned downstream of the pylorus sphincter such that the elongate collapsible tubular member extends through the pylorus sphincter.

Alternatively or additionally to any of the embodiments above, the first anchor is self-expandable from a collapsed delivery configuration to an expanded anchoring configuration.

Alternatively or additionally to any of the embodiments above, the second anchor is self-expandable from a collapsed delivery configuration to an expanded anchoring configuration.

Alternatively or additionally to any of the embodiments above, the elongate collapsible tubular member is biased to a collapsed configuration in which a lumen extending through the elongate collapsible tubular member is closed.

An apparatus for protecting against leaks within a portion of a patient's gastrointestinal tract is disclosed. The gastrointestinal tract includes a sphincter that is configured to reversibly close the gastrointestinal tract proximate the sphincter. The apparatus has an upstream end and a downstream end. An upstream anchor is disposed relative to the upstream end of the apparatus and configured to anchor at a position upstream from the sphincter. A downstream anchor is disposed relative to the downstream end of the apparatus and is configured to anchor at a position downstream from the sphincter. An elongate collapsible tubular member extends from the upstream anchor to the downstream anchor and thus extends through the sphincter. The elongate collapsible tubular member includes a collapsible lumen extending therethrough such that the sphincter can close the elongate collapsible tubular member proximate the sphincter by collapsing the collapsible lumen.

Alternatively or additionally to any of the embodiments above, the elongate collapsible tubular member includes a silicone tube.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The disclosure may be more completely understood in consideration of the following description of in connection with the accompanying drawings, in which:

FIG. 11 is a schematic illustration of the apparatus of FIG. 3, shown disposed within a portion of the person's gastrointestinal tract with the lower esophageal and pylorus sphincters in constricted configurations.

Figure 1:
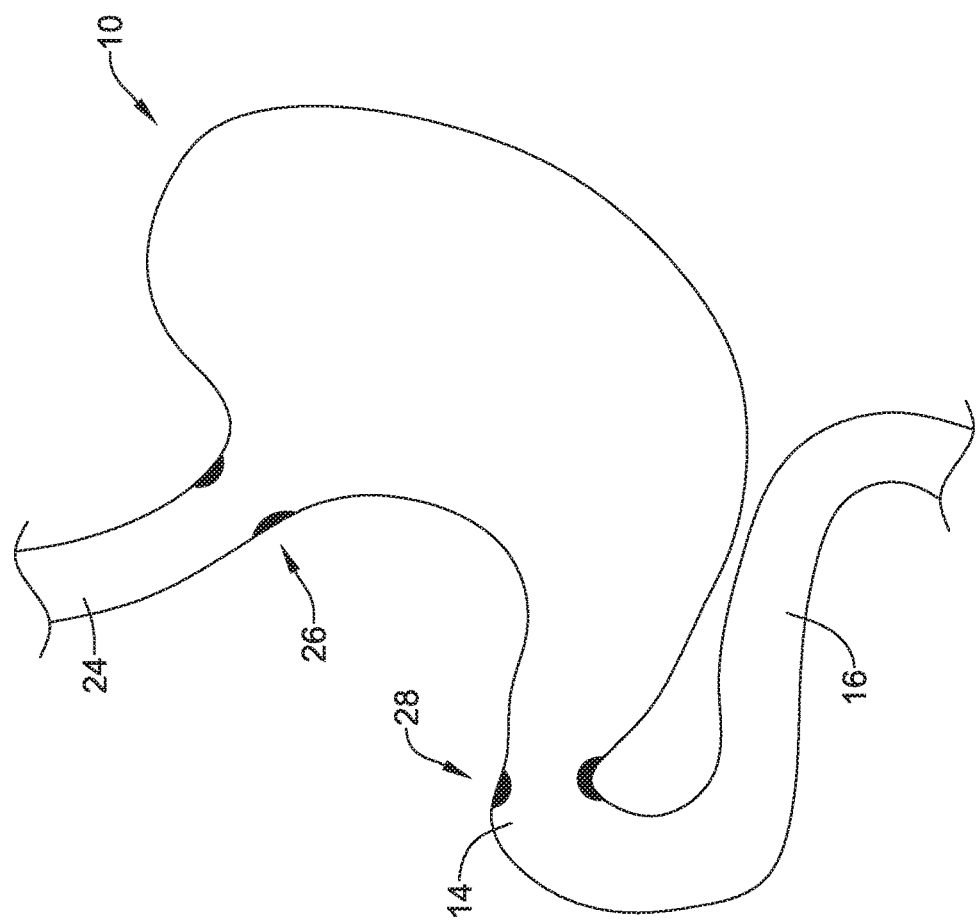
FIG. 1 is a schematic illustration of a portion of a person's gastrointestinal tract.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

There are a number of conditions, diseases and surgical interventions that may result in wounds such as an abscess within the gastrointestinal tract. In many cases, a surgical intervention may create a staple line or suture line within a portion of the gastrointestinal tract. An illustrative but non-limiting example of such a surgical intervention is bariatric surgery. In bariatric surgery, which may be performed as an open surgery or more commonly as a laproscopic surgery, an obese patient's stomach is made substantially smaller. As a result, the patient may be able to lose weight, particularly if they follow corresponding dietary restrictions. There are several common bariatric techniques, including but not limited to a sleeve gastrectomy and a Roux-en-Y gastric bypass procedure.

FIG. 1 provides an illustration of a patient's stomach 10. The stomach 10 extends distally from an esophagus 24 to a small intestine 16 via a pylorus 14. It will be appreciated that the stomach 10, the esophagus 24 and the small intestine 16 may be considered as forming a portion of the patient's gastrointestinal (GI) tract. The esophagus 24 includes a lower esophageal sphincter 26, which is shown schematically. The lower esophageal sphincter 26 is a ring of muscles that can be relaxed to provide an opening therethrough and that can be tightened to close against the flow of materials. Control of the lower esophageal sphincter 24 is largely involuntary. When the person is not eating or drinking, the lower esophageal sphincter 26 is generally closed to prevent stomach contents, including gastric acid, from moving upward into the esophagus 24 where it can cause damage. As the person swallows, the lower esophageal sphincter 26 can temporarily relax, or open, to allow swallowed nutritional content such as food and beverages, to pass into the stomach 10. A pylorus sphincter 28 is located near the entrance to the pylorus 14. The pylorus sphincter 28 is also a ring of muscles that can be relaxed to provide an opening therethrough and that can be tightened to close against the flow of materials. The pylorus sphincter 28 may be opened and closed to control the passage of stomach contents from the stomach 10 to the small intestine 16. Control of the pylorus sphincter 28 is largely involuntary.

Figure 2:
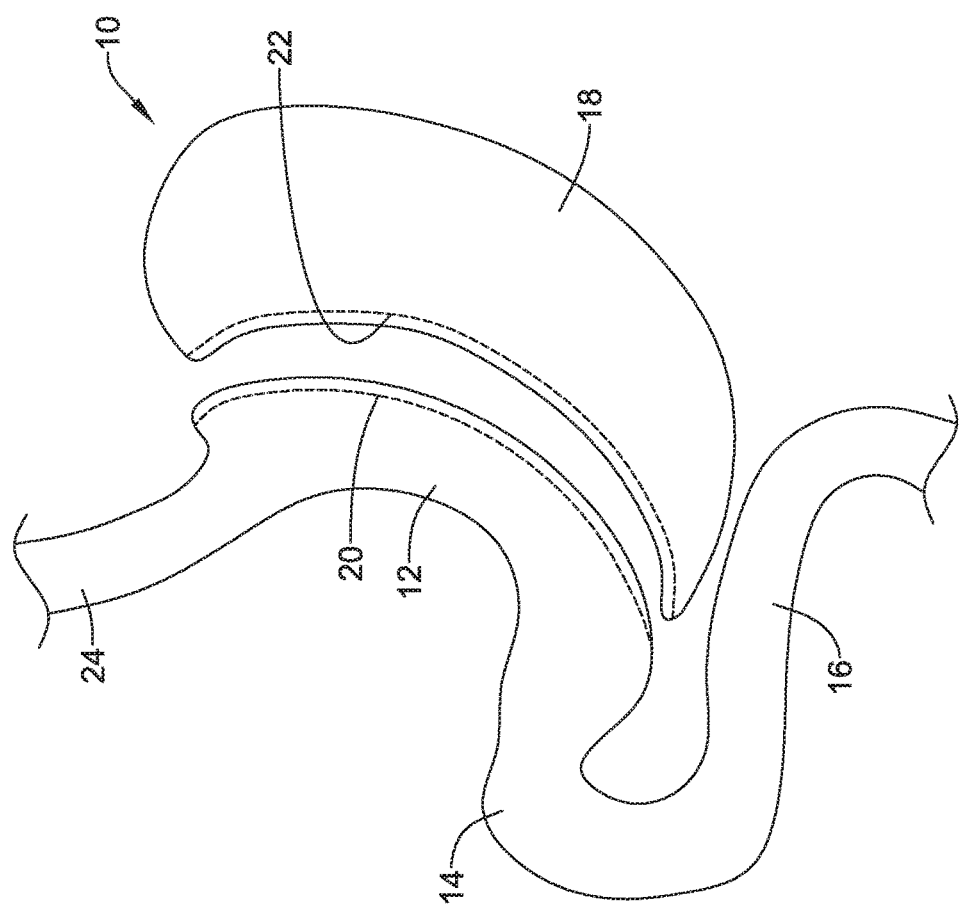
FIG. 2 is a schematic illustration of a gastric sleeve procedure.

FIG. 2 illustrates the results of a procedure known as sleeve gastrectomy, in which a large portion of the patient's stomach 10 is cut away. As a result, a relatively small attached portion 12 of the patient's stomach 10 remains fluidly coupled through the pylorus 14 with the small intestine 16. As can be seen in FIG. 1, a relatively large resected portion 18 of the patient's stomach 10 is resected, or cut away from the attached portion 12 of the stomach 10 that remains as part of the patient's effective gastrointestinal tract and extends from the esophagus 24 to the small intestine 16. It will be appreciated that as a result of the resection, a large staple line 20 is formed along one side of the small portion 12 of the stomach 10. A corresponding long staple line 22 is formed along one side of the resected portion 16 of the stomach 10. The disclosure provides devices that may, for example, be used to isolate the staple line 20 from nutritional contents passing through the attached portion 12 of the stomach 10.

Figure 3:
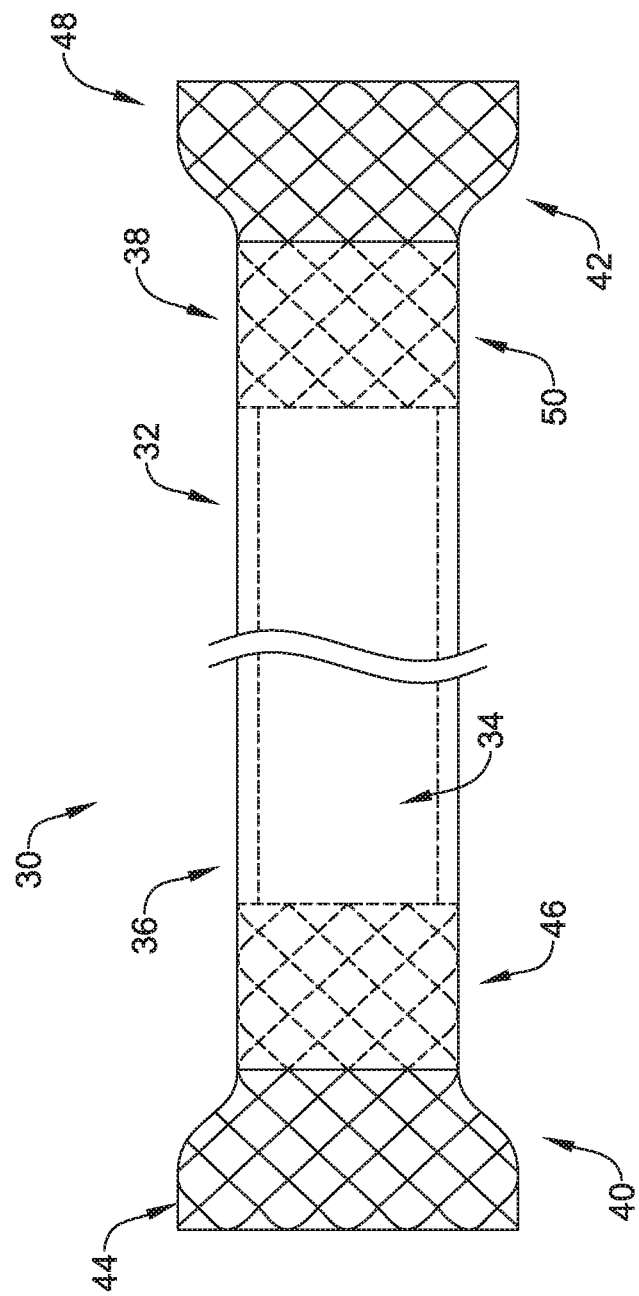
FIG. 3 is a schematic illustration of an apparatus that may be used in conjuncture with a procedure such as that shown in FIG. 2.

FIG. 3 is a schematic illustration of an apparatus 30 that may, for example, be considered as being useful for protecting against leaks after a surgical procedure on the stomach 10, such as but not limited to the gastric bypass procedure illustrated in FIG. 2. The apparatus 30 may include an elongate collapsible tubular member 32 defining a collapsible lumen 34 that extends through the elongate collapsible tubular member 32 from a proximal region 36 to a distal region 38.

The apparatus 30 may include an expandable proximal anchor 40 that is secured to the proximal region 36 of the elongate collapsible tubular member 32. The expandable proximal anchor 40 may, as illustrated in FIG. 3, be considered as being in its radially expanded configuration. As with most stent and stent-like structures, the expandable proximal anchor 40 may be constricted or otherwise radially compressed for delivery. In some cases, the expandable proximal anchor 40 may be configured to anchor at a first position above the lower esophageal sphincter 26 (FIG. 1). For example, the expandable proximal anchor 40 may have an overall dimension that provides a sufficient radial force to hold the expandable proximal anchor 40 in position.

The apparatus 30 may include an expandable distal anchor 42 that is secured to the distal region 38 of the elongate collapsible tubular member 32. The expandable distal anchor 42 may, as illustrated in FIG. 3, be considered as being in its radially expanded configuration. As with most stent and stent-like structures, the expandable distal anchor 42 may be constricted or otherwise radially compressed for delivery. In some cases, the expandable distal anchor 42 may be configured to anchor at a second position below the pylorus sphincter 28 (FIG. 1). For example, the expandable distal anchor 42 may have an overall dimension that provides a sufficient radial force to hold the expandable distal anchor 42 in position.

While the expandable proximal anchor 40 and the expandable distal anchor 42 are illustrated as being roughly the same size, it will be appreciated that in some cases the relative sizes of the expandable proximal anchor 40 and/or the expandable distal anchor 42 may be varied in order to accommodate particular features of the patient's anatomy. In some cases, the expandable proximal anchor 40 may have an overall diameter, when expanded, that is in the range of 20 millimeters (mm) to 35 millimeters (mm), 23 millimeters (mm) to 33 mm, or 25 millimeters (mm) to 30 millimeters (mm), for example. In some cases, the expandable distal anchor 42 may have an overall diameter, when expanded, that is in the range 20 millimeters (mm) to 35 millimeters (mm), 22 millimeters (mm) to 32 mm, or 25 millimeters (mm) to 30 millimeters (mm), for example. In some embodiments the diameter of the proximal anchor 40 in its expanded state may be greater than the diameter of the distal anchor 42 in its expanded state to accommodate the patient's anatomy.

In some cases, as illustrated, the expandable proximal anchor 40 may include a wider tissue engagement portion 44 that is configured to engage tissue and a narrower portion 46 that is configured to engage the proximal region 36 of the elongate collapsible tubular member 32. In some cases, for example, the elongate collapsible tubular member 32 may be secured to the expandable proximal anchor 40 by stretching the proximal region 36 of the elongate collapsible tubular member 32 over the narrower portion 46. In some cases, an adhesive may also be used to secure the elongate collapsible tubular member 32 to the expandable proximal anchor 40.

In some cases, as illustrated, the expandable distal anchor 42 may include a wider tissue engagement portion 48 that is configured to engage tissue and a narrower portion 50 that is configured to engage the distal region 38 of the elongate collapsible tubular member 32. In some cases, for example, the elongate collapsible tubular member 32 may be secured to the expandable distal anchor 42 by stretching the distal region 38 of the elongate collapsible tubular member 32 over the narrower portion 50. In some cases, an adhesive may also be used to secure the elongate collapsible tubular member 32 to the expandable distal anchor 42.

In some cases, the expandable proximal anchor 40 and the expandable distal anchor 42 may be considered as being stents and may be formed of any desired metallic or polymeric material. In some cases, the expandable proximal anchor 40 and the expandable distal anchor 42 may be formed of a bioabsorbable material that will simply disappear in time within the body. As illustrated, the expandable proximal anchor 40 and the expandable distal anchor 42 are braided stents. In some cases, the expandable proximal anchor 40 and/or the expandable distal anchor 42 may be woven stents or laser cut stents.

Figure 4:
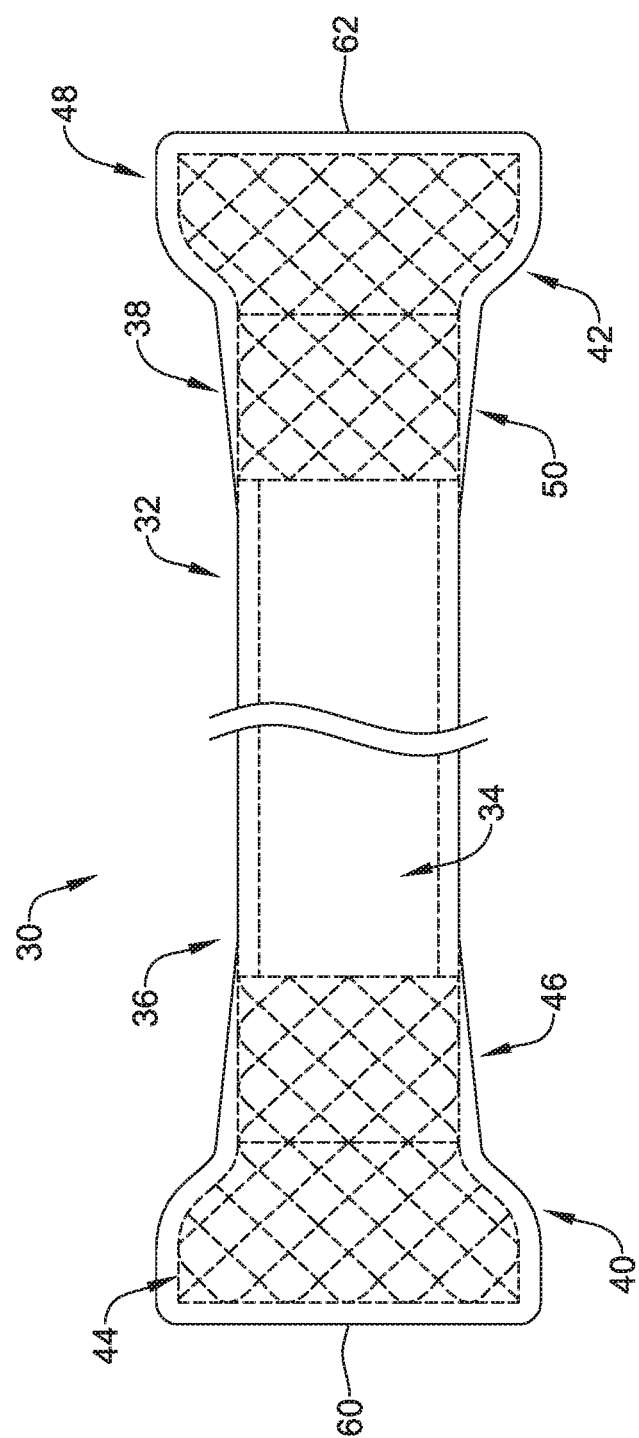
FIG. 4 is a schematic illustration of the apparatus of FIG. 3, including a polymeric covering disposed over the anchor structures.

In some cases, and with brief reference to FIG. 4, the expandable proximal anchor 40 may include a polymeric covering 60 that covers at least part of or the entire circumference of the expandable proximal anchor 40. In some cases, the expandable distal anchor 42 may similarly include a polymeric covering 62 that covers at least part of or the entire circumference of the expandable distal anchor 42. In some cases, the coverings 60, 62 may be formed of a low durometer silicone or polyurethane, for example. For instance, the coverings 60, 62 may be formed of a polymeric material having a Shore durometer hardness reading of 60 A or less, 50 A or less, 40 A or less, 30 A or less, or 20 A or less in some embodiments.

Returning to FIG. 3, the elongate collapsible tubular member 32 may have an overall length that is sufficient to place the expandable proximal anchor 40 above a sphincter such as but not limited to the lower esophageal sphincter 26 (FIG. 1) and to place the expandable distal anchor 42 below a sphincter such as but not limited to the pylorus sphincter 28 (FIG. 1). In some cases, the elongate collapsible tubular member 32 may have a length that is in the range of 15 centimeters (cm) to 25 cm. The apparatus 30 may have an overall length that is that is in the range of 25 cm to 35 cm. The elongate tubular member 32 may have a diameter (when not collapsed) of 20 millimeters (mm) to 30 millimeters, for example.

Figure 5:
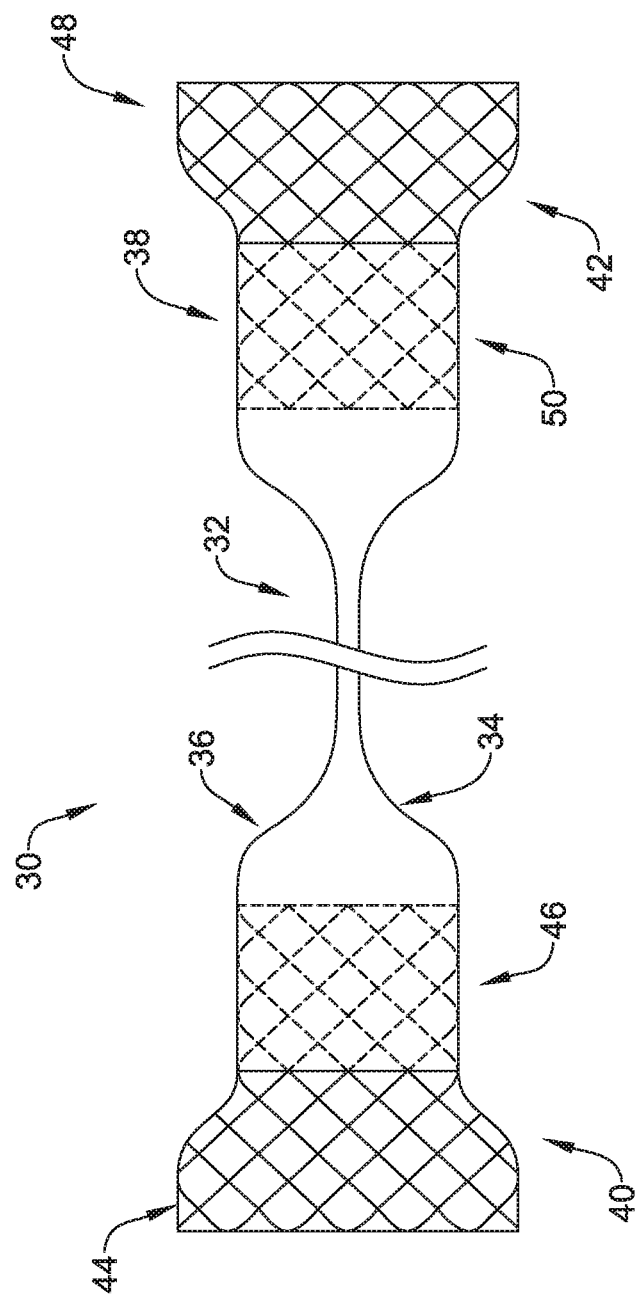
FIG. 5 is a schematic illustration of the apparatus of FIG. 3, shown in a collapsed configuration.

In some cases, as shown for example in FIG. 5, the elongate collapsible tubular member 32 may be considered as being biased to a collapsed configuration. In some cases, the elongate collapsible tubular member 32 may be considered as collapsing under its own weight, thereby causing the collapsible lumen 34 (FIG. 3) to close itself off whenever there is no nutritional contents moving down through the collapsible lumen 34. The elongate collapsible tubular member 32 may be formed of a polymeric material having a Shore durometer hardness reading of 60 A or less, 50 A or less, 40 A or less, 30 A or less, or 20 A or less in some instances. In some cases, the elongate collapsible tubular member 32 may be formed of silicone or polyurethane, although other polymers are contemplated. In some cases, the elongate collapsible tubular member 32 may be formed of a bioabsorbable material that will simply disappear over time in the body. In some instances, the elongate collapsible tubular member 32, along with the proximal and distal anchors 40, 42, may be formed of a bioabsorbable material, however, in other instances the elongate collapsible tubular member 32 may be formed of a bioabsorbable material while the proximal and distal anchors 40, 42 may be formed of a biostable material. Thus, after the elongate collapsible tubular member 32 has been fully absorbed by the patient's body, the proximal and/or distal anchors 40, 42 may be removed from the patient's body, if desired.

Figure 6:
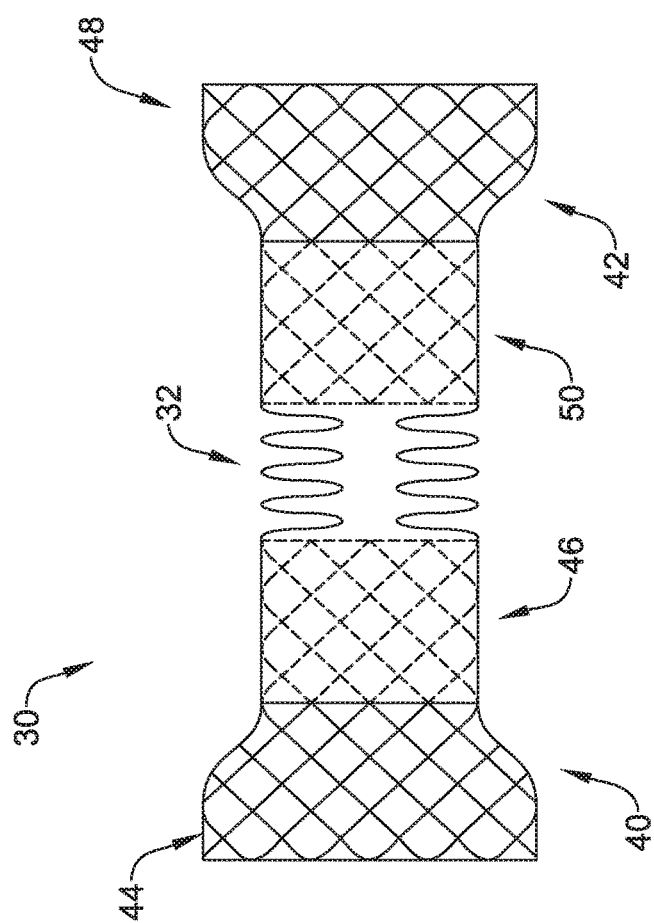
FIG. 6 is a schematic illustration of the apparatus of FIG. 3, shown in an axially collapsed configuration such as may be used for delivery.

In some instances, as shown for example in FIG. 6, the apparatus 30 may be axially compressible or collapsible. As shown, the expandable proximal anchor 40 is quite close to the expandable distal anchor 42, and the elongate collapsible tubular member 32 is folded up accordion-style between the expandable proximal anchor 40 and the expandable distal anchor 42. In some cases, this configuration may be useful in delivering the apparatus 30 via a catheter extended through an endoscope. The catheter may be advanced into position proximate the pylorus sphincter 28 (FIG. 1), such as distal of the pylorus sphincter 28, for example, and an outer sheath may be withdrawn proximally to allow the expandable distal anchor 42 to expand and engage tissue distal of the pylorus sphincter 28. The catheter may then be withdrawn proximally until the expandable proximal anchor 40 is positioned proximate the lower esophageal sphincter 26 (FIG. 1), such as proximal of the lower esophageal sphincter 26, for example, and the outer sheath may be withdrawn proximally to allow the expandable proximal anchor 40 to expand and engage tissue proximal of the lower esophageal sphincter 26. It will be appreciated that this particular delivery technique is merely illustrative.

Figure 7:
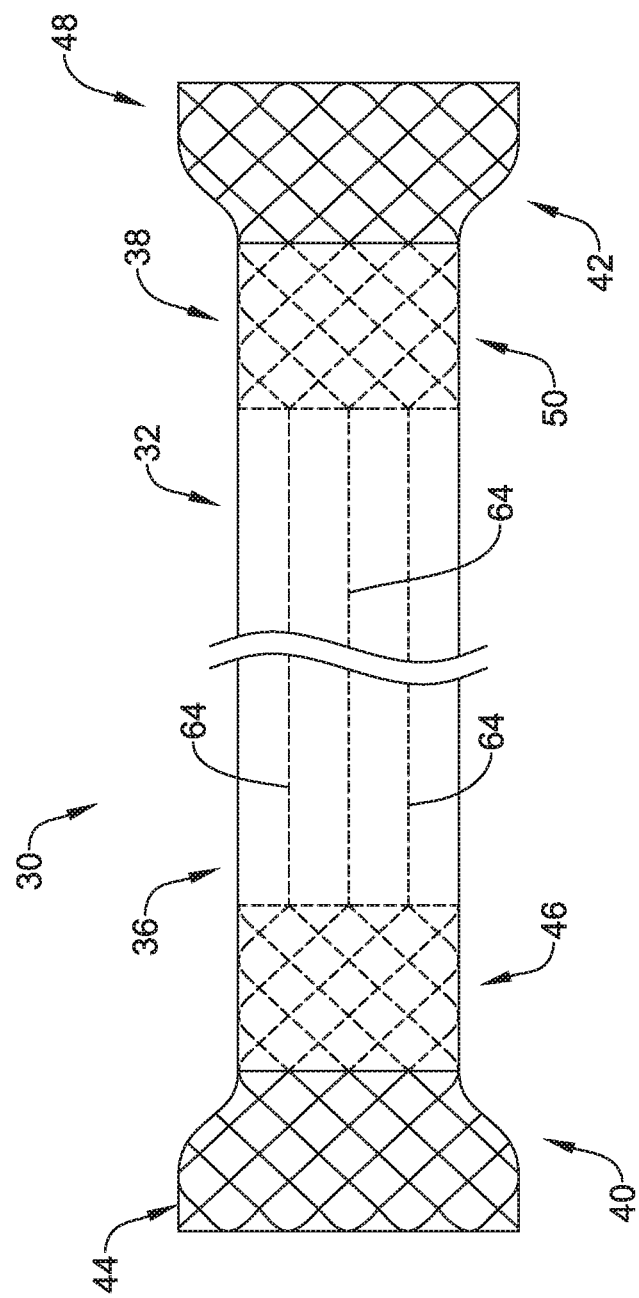
FIG. 7 is a schematic illustration of the apparatus of FIG. 3, including a wire support member.
Figure 8:
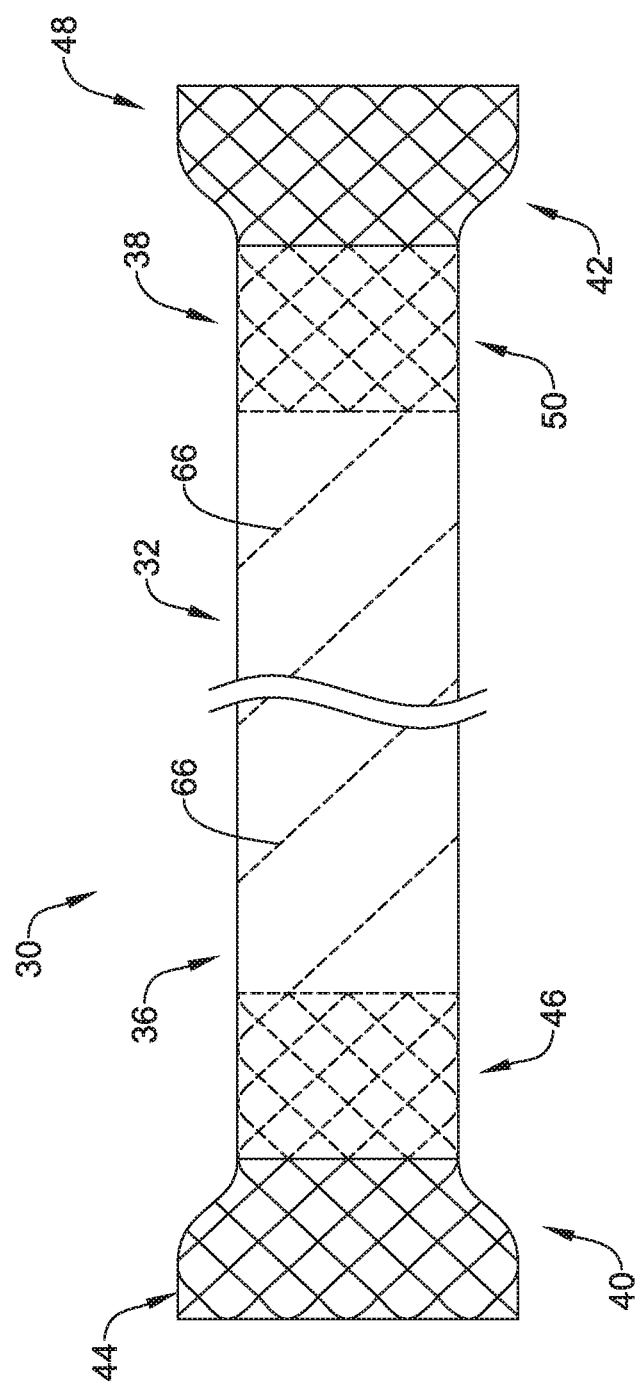
FIG. 8 is a schematic illustration of the apparatus of FIG. 3, including a wire support member.

In some cases, there may be a desire to provide some structure to the elongate collapsible tubular member 32. FIGS. 7 and 8 provide illustrative, but non-limiting examples of wire supports that may be incorporated into the elongate collapsible tubular member 32 of the apparatus 30. In FIG. 7, several axially-aligned wire supports 64 extend longitudinally along the length of the elongate collapsible tubular member 32 from the expandable proximal anchor 40 to the expandable distal anchor 42. In FIG. 8, several helically aligned wire supports 66 are shown extending helically along the length of the elongate collapsible tubular member 32 from the expandable proximal anchor 40 to the expandable distal anchor 42. In some cases, the wire supports 64 and/or the wire supports 66 are disposed inside the collapsible lumen 34 (FIG. 3) (i.e., along an inner surface of the polymer wall forming the elongate collapsible tubular member 32) or are embedded within the polymer wall forming the elongate collapsible tubular member 32, and thus are shown in phantom. In some cases, the wire supports 64 and/or the wire supports 66, if present, are configured to hold the collapsible lumen 34 open in the absence of externally applied forces, but are compliant enough that the collapsible lumen 34 is able to close in response to the lower esophageal sphincter 26 (FIG. 1) and/or the pylorus sphincter 28 (FIG. 1) constricting against the apparatus 30.

Figure 9:
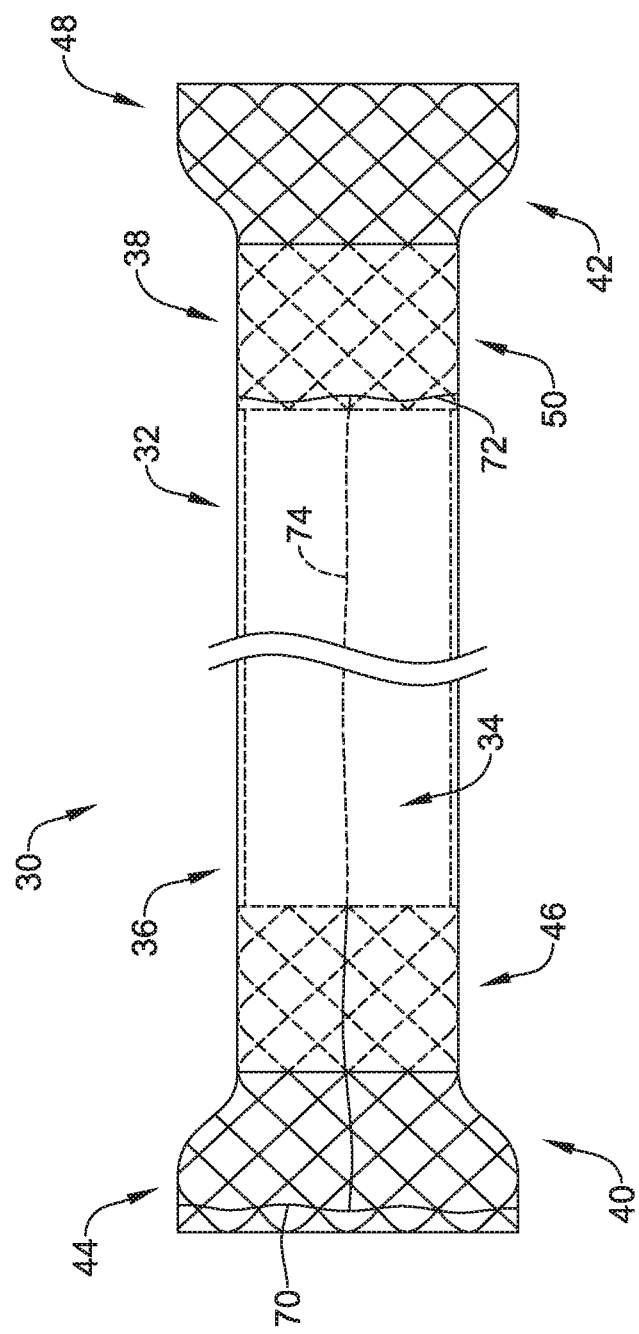
FIG. 9 is a schematic illustration of the apparatus of FIG. 3, including retrieval tethers.

In some cases, as shown for example in FIG. 9, the apparatus 30 may include features that enable re-positioning during deployment and/or that facilitate subsequent removal of the apparatus 30. In some cases, for example, the expandable proximal anchor 40 may include a tether 70 that extends around a circumference of the expandable proximal anchor 40. For example, the tether 70 may be a suture extending circumferentially around the proximal end of the expandable proximal anchor 40 configured to be grasped and pulled proximally to remove the expandable proximal anchor 40 from the patient. In some instances, the tether 70 may be woven through interstices of a woven structure of the expandable proximal anchor 40. In other instances, the tether 70 may be formed as a unitary portion of a filament forming the expandable proximal anchor 40. By providing a constricting force on the tether 70, it is possible to partially compress the expandable proximal anchor 40 for removal from the body lumen. Similarly, the expandable distal anchor 42 may include a tether 72 that extends around a circumference of the expandable distal anchor 42. For example, the tether 72 may be a suture extending circumferentially around the proximal end of the expandable distal anchor 42 configured to be grasped and pulled proximally to remove the expandable distal anchor 42 from the patient. In some instances, the tether 72 may be woven through interstices of a woven structure of the expandable distal anchor 42. In other instances, the tether 72 may be formed as a unitary portion of a filament forming the expandable distal anchor 42. By providing a constricting force on the tether 72, it is possible to partially compress the expandable distal anchor 42. In some instances, the tether 70 may be interconnected with the tether 72 such that pulling the tether 70 proximally simultaneously pulls the tether 72 to simultaneously collapse both the proximal expandable anchor 40 and the expandable distal anchor 42. For example, a tether 74 may extend longitudinally through the elongate collapsible tubular member 32, such as through the lumen 34, from the tether 70 to the tether 72. Thus, pulling the tether 70 proximally will likewise pull the longitudinally oriented tether 74 proximally within the collapsible tubular member 32 to in turn pull the tether 72 proximally to collapse the proximal and distal anchors 40, 42 simultaneously.

It will be appreciated that features shown in one Figure may be combined with features shown in other Figures. For example, the polymeric coverings 60, 62 shown in FIG. 4 may be combined with the tethers 70, 72 shown in FIG. 9. The wire supports 64 (FIG. 7) and/or the wire supports 66 (FIG. 8) may be combined with the tethers 70, 72 of FIG. 9 or with the polymeric coverings 60, 62 of FIG. 4.

Figure 10:
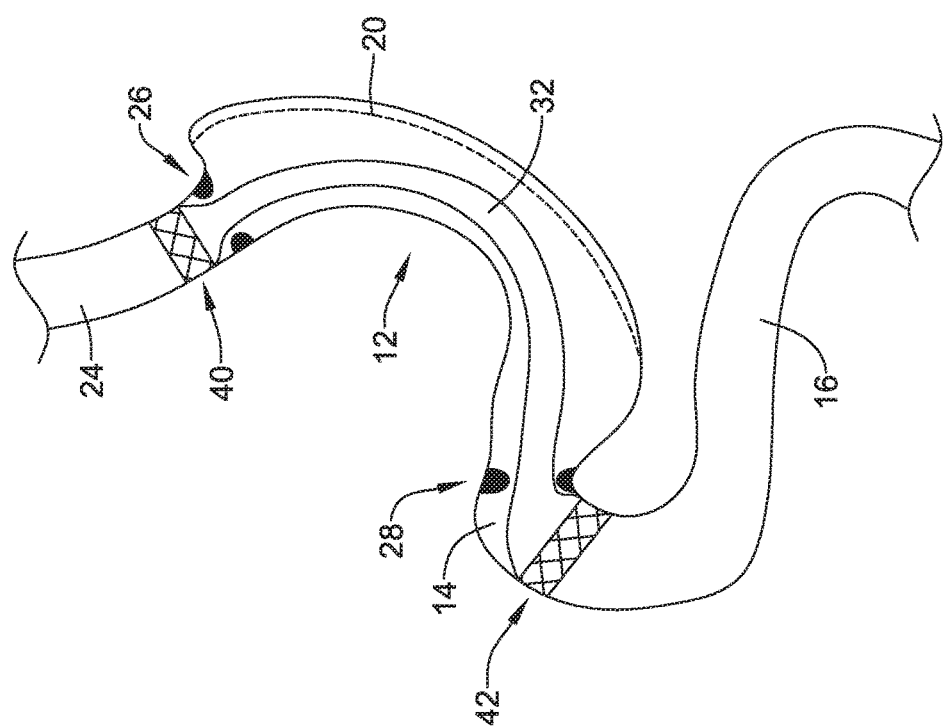
FIG. 10 is a schematic illustration of the apparatus of FIG. 3, shown disposed within a portion of the person's gastrointestinal tract with the lower esophageal and pylorus sphincters in relaxed configurations.

FIGS. 10 and 11 show the apparatus 30 disposed within the gastrointestinal tract, extending through the remaining stomach portion 12 with the expandable proximal anchor 40 disposed above (or upstream of) the lower esophageal sphincter 26 and the expandable distal anchor 42 disposed below (or downstream of) the pylorus sphincter 28. In FIG. 10, the elongate collapsible tubular member 32 is shown in a non-collapsed configuration with the lower esophageal sphincter 26 and the pylorus sphincter 28 both in their relaxed, or open configurations. In FIG. 11, both sphincters 26, 28 are in their constricted, or closed configurations, and the elongate collapsible tubular member 32 is shown in a collapsed configuration. While the sphincters 26, 28 are shown as either both open or both closed, it will be appreciated that in many cases these sphincters 26, 28 will open and close independently of each other.

It will be appreciated that a variety of different materials may be used in forming the apparatus 30. In some embodiments, for example, the polymeric covering 60, 62 may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85 A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50 A), polycarbonates, ionomers, biocompatible polymers, other suitable materials, or mixtures, combinations, copolymers thereof, polymer/metal composites, and the like.

The expandable proximal anchor 40 and the expandable distal anchor 42 may be formed of any suitable desired material, such as a biocompatible material including biostable, bioabsorbable, biodegradable or bioerodible materials. For instance, the expandable framework may be formed of a polymeric material or a metallic material. Some suitable polymeric materials are listed above. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the expandable framework may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In some embodiments, the apparatus 30 may be coated with or otherwise include an elutable drug. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An apparatus for protecting against leaks after a surgical procedure on a stomach, the apparatus configured to extend through the stomach once implanted, the apparatus comprising:
    an elongate collapsible tubular member having a proximal region and a distal region and a collapsible lumen extending therethrough;
    an expandable proximal anchor including only a single wide proximal tissue engagement portion connected to a single narrow distal portion, the narrow distal portion secured to the proximal region of the elongate collapsible tubular member, the expandable proximal anchor configured to anchor at a first position above a lower esophageal sphincter;
    an expandable distal anchor secured to the distal region of the elongate collapsible tubular member, the expandable distal anchor including a wide tissue engagement portion and a narrow portion, the expandable distal anchor configured to anchor at a second position below a pylorus sphincter;
    a proximal end of the elongate collapsible tubular member extending proximally only over the narrow portion of the expandable proximal anchor such that the proximal end of the elongate collapsible member is located distal of the wide tissue engagement portion of the expandable proximal anchor and a distal end of the elongate collapsible tubular member extending distally only over the narrow portion of the expandable distal anchor such that the distal end of the elongate collapsible member is located proximal of the wide tissue engagement portion of the expandable distal anchor.

2. The apparatus of claim 1, wherein the expandable proximal anchor comprises a braided stent and a covering disposed over at least part of the braided stent.

3. The apparatus of claim 1, wherein the expandable distal anchor comprises a braided stent and a covering disposed over at least a part of the braided stent.

4. The apparatus of claim 1, further comprising a removal tether extending around a circumference of the expandable proximal anchor.

5. The apparatus of claim 1, further comprising a removal tether extending around a circumference of the expandable distal anchor.

6. The apparatus of claim 1, wherein the apparatus is bio-absorbable.

7. The apparatus of claim 1, further comprising a wire support extending at least partially along the elongate collapsible tubular member.

8. The apparatus of claim 7, wherein the wire support extends from the expandable proximal anchor to the expandable distal anchor.

9. The apparatus of claim 7, wherein the wire support is embedded in the elongate collapsible tubular member.

10. The apparatus of claim 7, wherein the wire support extends helically along the elongate collapsible tubular member.

11. The apparatus of claim 1, wherein the elongate collapsible tubular member is formed of a polymer having a Shore durometer hardness of 60 A or less.

12. The apparatus of claim 1, wherein the expandable proximal and distal anchors each comprise a braided stent, wherein the elongate collapsible tubular member defines a collapsing region between a distal end of the expandable proximal anchor and a proximal end of the expandable distal anchor that is devoid of the braided stent of first and second anchors.

13. The apparatus of claim 12, wherein the collapsing region of the elongate collapsible tubular member collapses under its own weight to close off the collapsible lumen whenever nutritional contents are not moving through the collapsible lumen.

14. The apparatus of claim 13, wherein the elongate tubular member has a length of between 15 cm to 25 cm.

15. An apparatus for protecting against leaks within a portion of a gastrointestinal tract, the gastrointestinal tract including a sphincter that is configured to reversibly close the gastrointestinal tract proximate the sphincter, the apparatus comprising:
    an elongate collapsible tubular member having a first end and a second end and a collapsible lumen extending therethrough;
    a first anchor secured near the first end of the elongate collapsible tubular member, the first anchor configured to anchor at a position upstream from the sphincter;
    a second anchor secured near the second end of the elongate collapsible tubular member, the second anchor configured to anchor at a position downstream from the sphincter;
    wherein the elongate collapsible tubular member is biased in a collapsed configuration such that the elongate collapsible tubular member collapses under its own weight to close off the collapsible lumen.

16. The apparatus of claim 15, wherein the first anchor is self-expandable from a collapsed delivery configuration to an expanded anchoring configuration.

17. The apparatus of claim 15, wherein the second anchor is self-expandable from a collapsed delivery configuration to an expanded anchoring configuration.

18. The apparatus of claim 15, wherein the elongate collapsible tubular member is axially collapsible to move the first anchor toward the second anchor.

19. An apparatus for protecting against leaks within a portion of a gastrointestinal tract, the gastrointestinal tract including a sphincter that is configured to reversibly close the gastrointestinal tract proximate the sphincter, the apparatus having an upstream end and a downstream end, the apparatus comprising:
    an upstream anchor disposed relative to the upstream end of the apparatus and configured to secure the apparatus within the gastrointestinal tract with the upstream anchor disposed at a position upstream from the sphincter;
    a downstream anchor disposed relative to the downstream end of the apparatus and configured to secure the apparatus within the gastrointestinal tract with the downstream anchor disposed at a position downstream from the sphincter; and an elongate collapsible tubular member extending from the upstream anchor to the downstream anchor and thus extending through the sphincter, the elongate collapsible tubular member including a collapsible lumen extending therethrough such that the sphincter can close the elongate collapsible tubular member proximate the sphincter by collapsing the collapsible lumen, the elongate collapsible tubular member having a length of between 15 cm to 25 cm;

wherein the elongate collapsible tubular member has an outermost diameter less than an outermost diameter of the upstream anchor and less than an outermost diameter of the downstream anchor.

20. The apparatus of claim 19, wherein the elongate collapsible tubular member comprises a silicone tube having a collapsing region defined between the upstream anchor and the downstream anchor, wherein the collapsing region of the elongate collapsible tubular member collapses under its own weight to close off the collapsible lumen whenever nutritional contents are not moving through the collapsible lumen.

* * * * *